US00PP14588P29

(12) United States Plant Patent
Hansson

(10) Patent No.: US PP14,588 P2
(45) Date of Patent: Mar. 9, 2004

(54) RHIPSALIDOPSIS PLANT NAMED 'CEBEMMA'

(50) Latin Name: *Rhipsalidopsis gaertneri*
Varietal Denomination: Cebemma

(76) Inventor: Jorn Hansson, Holmevej 36, 5471 Sondersoe (DK)

( * ) Notice: Subject to any disclaimer, the term of this patent is extended or adjusted under 35 U.S.C. 154(b) by 0 days.

(21) Appl. No.: 10/396,682

(22) Filed: Mar. 25, 2003

(51) Int. Cl.[7] ..... A01H 5/00
(52) U.S. Cl. ..... Plt./372
(58) Field of Search ..... Plt./372

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Rhipsalidopsis plant named 'Cebemma', characterized by its compact, upright and outwardly spreading plant habit; freely branching growth habit; and freely flowering with white-colored flowers.

1 Drawing Sheet

Botanical classification/cultivar designation: *Rhipsalidopsis gaertneri* cultivar Cebemma.

BACKGROUND OF THE INVENTION

The present Invention relates to a new and distinct cultivar of Rhipsalidopsis plant, botanically known as *Rhipsalidopsis gaertneri*, and hereinafter referred to by the name 'Cebemma'.

The new Rhipsalidopsis is a product of a planned breeding program conducted by the Inventor in Odense, Denmark. The objective of the breeding program is to create new compact Rhipsalidopsis with good postproduction longevity.

The new Rhipsalidopsis originated from a cross-pollination in April, 1995, of two proprietary seedling selections of *Rhipsalidopsis gaertneri*, not patented. The new Rhipsalidopsis was discovered and selected as a single plant from the resulting progeny of the cross-pollination by the Inventor in a controlled environment in Odense, Denmark, in March, 1998.

Asexual reproduction of the new cultivar by cuttings taken at Odense, Denmark, since May, 1998, has shown that the unique features of this new Rhipsalidopsis are stable and reproduced true to type in successive generations.

SUMMARY OF THE INVENTION

Plants of the cultivar Cebemma have not been observed under all possible environmental conditions. The phenotype may vary somewhat with variations in environment such as temperature and/or light intensity without, however, any variance in genotype.

The following traits have been repeatedly observed and are determined to be the unique characteristics of 'Cebemma'. These characteristics in combination distinguish 'Cebemma' as a new and distinct cultivar:

1. Compact, upright and outwardly spreading plant habit.
2. Freely branching growth habit.
3. Freely flowering with white-colored flowers.

Plants of the new Rhipsalidopsis differ from plants of the parent selections primarily in flower color as plants of the parent selections have pale pink-colored flowers.

Plants of the new Rhipsalidopsis can be compared to plants of the cultivar Auriga, not patented. In side-by-side comparisons conducted in Odense, Denmark, plants of the new Rhipsalidopsis differed primarily from plants of the cultivar Auriga in flower color as plants of the cultivar Auriga had orange red-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new Rhipsalidopsis.

The photograph at the top of the sheet comprises a side perspective view of a typical plant of 'Cebemma'.

The photograph at the bottom of the sheet comprises a close-up view of typical flowers of 'Cebemma'.

DETAILED BOTANICAL DESCRIPTION

In the following description, color references are made to The Royal Horticultural Society Colour Chart, 2001 Edition, except where general terms of ordinary dictionary significance are used. Plants used for the above-mentioned photographs and botanical description were grown in Odense, Denmark in 9-cm containers in a glass-covered greenhouse. During the production of the plants, day temperatures were about 16 to 18° C. and night temperatures were about 16° C. Plants used were about one year old when the photographs and description were taken.

Botanical classification: *Rhipsalidopsis×haylodgensis* cultivar Cebemma.

Parentage:

*Female, or seed, parent.*—Proprietary seedling selection of *Rhipsalidopsis gaertneri*, not patented.

*Male, or pollen, parent.*—Proprietary seedling selection of *Rhipsalidopsis gaertneri*, not patented.

Propagation:

*Type.*—By cuttings.

*Time to initiate roots.*—About 12 days at 20° C.

*Time to produce a rooted young plant.*—About 60 days at 20° C.

*Root description.*—Fine; freely branching; whitish in color.

Plant description:

*Form.*—Compact, upright and outwardly spreading; rounded inverted triangle.

*Branching habit.*—Freely branching with one to two phylloclades developing at the apex of each phylloclade.

*Plant height, soil level to top of plant plane.*—About 15 to 20 cm.

*Plant width.*—About 15 to 20 cm.

*Phylloclade description.*—Length: About 4.5 to 5 cm. Width: About 2.5 to 3 cm. Thickness: About 1 to 3 mm. Shape: Oblong. Apex: Truncated. Base: Obtuse. Margin: Entire. Texture, upper and lower surfaces: Smooth, glabrous. Venation pattern: Pinnate. Color, upper and lower surfaces: 137A. Venation color, upper and lower surfaces: 137A.

Flower description:

*Flower type and habit.*—Single, symmetrical, star-shaped, tubular flowers; flowers produced apically. Flowers persistent. Very freely flowering, typically about one to three flowers per terminal. Flowers not fragrant.

*Natural flowering season.*—Plants typically flower during April and May in Denmark; flowering recurrent.

*Flower longevity on the plant.*—About 10 to 15 days.

*Flower length.*—About 6 cm.

*Flower diameter.*—About 6 to 7 cm.

*Flower buds.*—Length: About 3.5 cm. Diameter: About 6.5 mm. Shape: Ovoid, pointed. Color: Close to 155D.

*Corolla.*—Quantity/arrangement: About 12 to 14 fused petals; funnelform. Petal length: About 3 to 4 cm. Petal width: About 6 to 8 mm. Petal shape: Elongated oblong to linear. Petal apex: Acute. Petal margin: Entire. Petal texture, upper and lower surfaces: Smooth, glabrous. Petal color, upper and lower surfaces: Close to 155D.

*Calyx.*—Shape: Rounded. Length: About 6 to 8 mm. Diameter: About 6 to 7 mm. Color: 137A.

*Reproductive organs.*—Stamens: Quantity per flower: About 20. Anther shape: Rounded. Anther length: About 1 mm. Anther color: 4D. Pollen amount: Scarce. Pollen color: 4D. Pistils: Quantity per flower: One. Pistil length: About 2 cm. Stigma shape: Star-shaped with five or six lobes. Stigma color: Close to 155D. Style length: About 1 to 1.2 cm. Style color: Close to 155D. Ovary color: 137C.

*Seeds/fruit.*—Seed and fruit production has not been observed.

Disease/pest resistance: Under commercial production conditions, plants of the new Rhipsalidopsis have not been noted to be resistant to pathogens or pests common to Rhipsalidopsis.

Temperature tolerance: Plants of the new Rhipsalidopsis have been observed to tolerate temperatures from about 4 to 28° C. in Odense, Denmark.

It is claimed:

1. A new and distinct cultivar of Rhipsalidopsis plant named 'Cebemma', as illustrated and described.

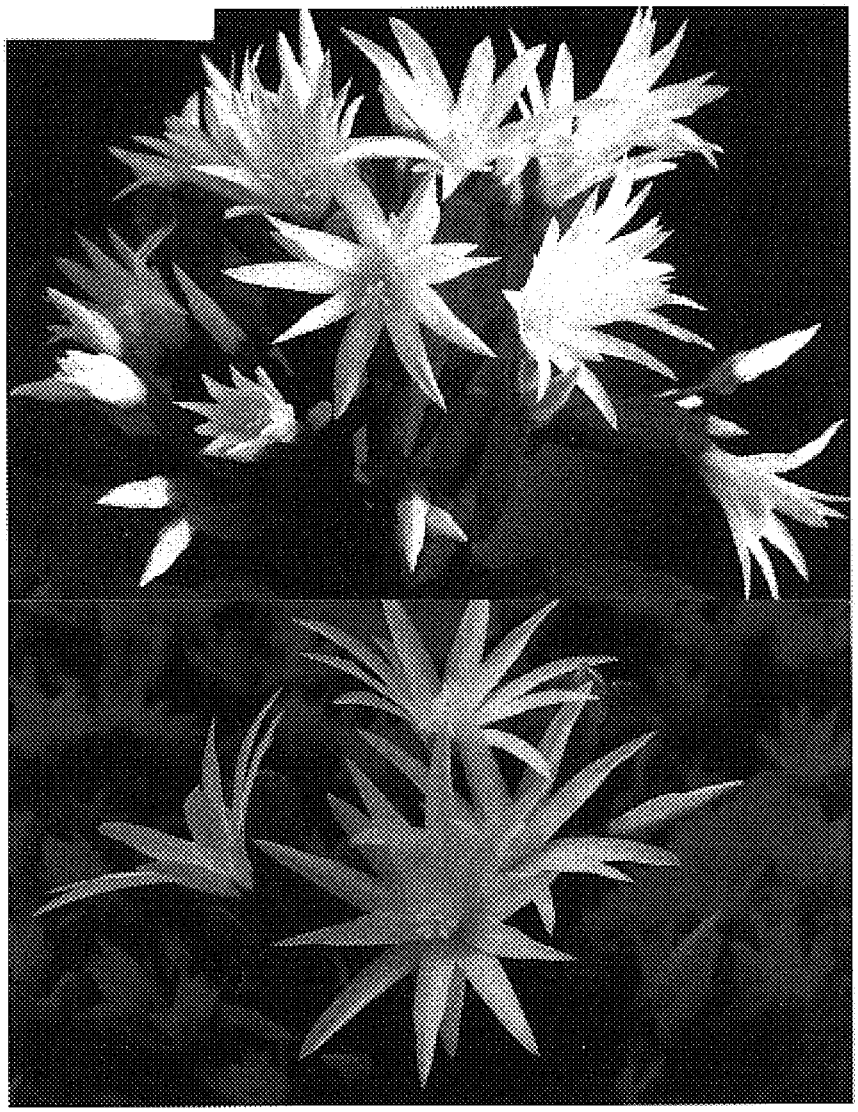

* * * * *